US011583379B2

(12) United States Patent
Chelle et al.

(10) Patent No.: US 11,583,379 B2
(45) Date of Patent: Feb. 21, 2023

(54) COMBINATION OF AN APPLICATOR AND OF A SUSPENSION HAVING AN ACTIVE PRINCIPLE

(71) Applicant: AB7 Innovation S.A.S.U, Deyme (FR)

(72) Inventors: René Chelle, Deyme (FR); Arnaud Vilbert, Baziege (FR)

(73) Assignee: AB7 INNOVATION S.A.S.U., Deyme (FR)

( * ) Notice: Subject to any disclaimer, the term of this patent is extended or adjusted under 35 U.S.C. 154(b) by 572 days.

(21) Appl. No.: 16/613,050

(22) PCT Filed: May 3, 2018

(86) PCT No.: PCT/FR2018/000106
§ 371 (c)(1),
(2) Date: Nov. 12, 2019

(87) PCT Pub. No.: WO2018/206865
PCT Pub. Date: Nov. 15, 2018

(65) Prior Publication Data
US 2020/0197144 A1   Jun. 25, 2020

(30) Foreign Application Priority Data

May 12, 2017   (FR) ...................................... 1700513

(51) Int. Cl.
| *A61D 7/00* | (2006.01) |
| *A01N 25/12* | (2006.01) |
| *A01N 31/02* | (2006.01) |
| *A01N 65/16* | (2009.01) |
| *A01N 65/22* | (2009.01) |
| *A01N 65/40* | (2009.01) |
| *A46B 11/00* | (2006.01) |

(52) U.S. Cl.
CPC ............... *A61D 7/00* (2013.01); *A01N 25/12* (2013.01); *A01N 31/02* (2013.01); *A01N 65/16* (2013.01); *A01N 65/22* (2013.01); *A01N 65/40* (2013.01); *A46B 11/0041* (2013.01); *A46B 2200/1093* (2013.01)

(58) Field of Classification Search
CPC .......... A61D 7/00; A01N 25/12; A01N 31/02; A01N 65/16; A01N 65/22; A01N 65/40; A46B 11/0041; A46B 2200/1093; A61P 33/00; A61K 2800/87; A61K 8/34; A61M 35/003; A45D 19/00; A45D 24/02; A45D 24/26; A61Q 5/006; A61Q 5/02; A61Q 17/02
See application file for complete search history.

(56) References Cited

U.S. PATENT DOCUMENTS

| 4,850,729 A | 7/1989 | Kramer et al. |
| 4,865,482 A | 9/1989 | Van Landingham |
| 2009/0324520 A1 | 12/2009 | Cetti et al. |
| 2016/0000661 A1 | 1/2016 | Van et al. |

FOREIGN PATENT DOCUMENTS

| EP | 0557489 | 9/1993 |
| FR | 1248721 | 12/1960 |
| FR | 2366815 | 5/1978 |
| WO | 2005004972 | 1/2005 |
| WO | 2005058405 | 6/2005 |

*Primary Examiner* — Robert S Cabral
(74) *Attorney, Agent, or Firm* — Benoit & Cote, Inc.

(57) ABSTRACT

The present invention relates to a combination of a flexible container of the type with a brush and a tube enclosing a homogeneous suspension composed of an aqueous phase and of an oily phase which has at least one active principle, characterized in that the container has an applicator consisting of friction members suitable for applying said suspension at the outlet of an orifice onto a zone of the body of a subject to be treated, said suspension having a suitable viscosity allowing it to be distributed homogeneously via said members of said applicator.

14 Claims, 1 Drawing Sheet

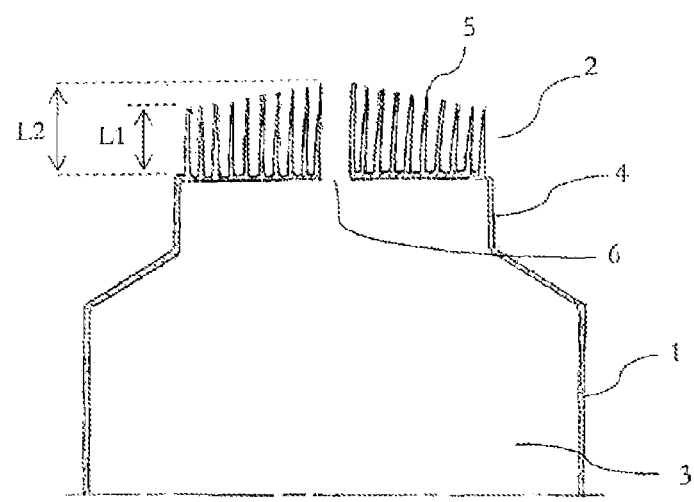

COMBINATION OF AN APPLICATOR AND OF A SUSPENSION HAVING AN ACTIVE PRINCIPLE

The present invention relates to a device for the distribution of product designed for the treatment of animals. More particularly, the present invention relates to a combination of a flexible container containing at least one active ingredient designed to be applied onto the body of an animal subject to be treated, an active ingredient the effectiveness of which involves a particular method of application.

It is known that a reduction of muscle tone in older animals can sometimes bring with it other discomforts such pain and tingling felt in different places of the body, particularly the muscles, joints and tendons. Among the muscular and joint pain observed in animals, arthritis affects around one in five dogs, in other words around 20% of the canine population whose average age is more than one year. It is also observed that arthritis affects not only older animals but also younger ones. Moreover, there will be an increase in cases of arthritis with the rise in the average life expectancy of dogs, as well as the increase in their average weight. In any event, arthritis penalizes the animal as regards its mobility, wellbeing and health.

In the search to improve the everyday comfort of our pets, but also of livestock and production animals, many products are available on the market that are designed in particular for anti-parasitic, repellant and anti-insect treatments.

It is recognized that anti-parasitic or anti-insect products in general, as well as pain-killing products, are available in all of the conventional pharmaceutical forms (spray, lotion, cream, gel, etc.). There is therefore a need, for the application of these products onto the body of an animal, for a manual intervention, particularly by massaging movements, in order to properly distribute them over the areas of the body to be treated.

To accompany this manual intervention, there are applicators from which the product, contained in a container, is directly distributed onto the area of the body to be treated. For example, the principle of a rotating ball closing the end of a tube, called a roll-on, is known which means that, for a good distribution of the product, the latter must be a liquid.

European Patent No. 0202359 proposes a combination of a two-compartment container with flexible walls, the first containing a compound with the consistency of a gel, and the second containing a compound with the consistency of a paste, the combination of these two compounds constitutes the composition. Said gel comprises hydrogen peroxide, cross-linked acrylic acid copolymer, polyol and water; its viscosity being sufficient to support itself on the bristles of a toothbrush. The paste may contain stabilizing and smoothing agents in the form of mineral powder such as bentonite and silica. The gel and paste must be combined immediately before oral use.

Also, European Patent No 0493553 describes a system of packaging, in a container, gel containing a pesticide; said gel being contained in a water-soluble bag before being placed in said container. The main object is to prevent the insecticide from leaking from the container. Along the same lines, European Patent No. 01774896 describes a system of packaging that comprises a water-dispersible gel formulation contained in a water-soluble bag, said gel containing a mineral particulate filler and an insecticide, fungicide or herbicide; the gel having an apparent average viscosity of 300 centipoises.

American Patent No. 2017/0007005 describes a gel dispenser housed in a flexible container, then distributed via an applicator provided with a slotted outlet valve, the opening/closing of which is operated by the pressure exerted on said container.

American U.S. Pat. No. 4,865,482 describes an anti-ectoparasitic brush having a container with a deformable wall and a liquid content. The brush consists of a plurality of bristles of identical length. French Patent No. 2366815 describes a brush formed of a frame from which solid bristles of identical length extend as well as one hollow tubular metal bristle in communication with a reservoir of liquid arranged in the frame. French Patent No. 1248721 describes an applicator of liquid products, creams or pastes. The applicator has tufts made of bristles or fibers; a reservoir with deformable walls is connected to the applicator. International Patent No. 2005/058405 describes a device for the application of liquid product, said device consisting of a reservoir with a deformable wall and an applicator surmounted by a sponge. American U.S. Pat. No. 4,850,729 describes a system for the distribution of decontaminating substances consisting of aqueous constituents and dry constituents, both packaged separately in a single reservoir. The system has an applicator surmounted by a sponge.

It should be noted that the hair of an animal represents a physical barrier to an application of a topical-action active ingredient in the sense that, in order to achieve good efficiency, it is necessary to part the hairs in order to reach the skin. At the same time, a product containing a repellent-action active ingredient, particularly an anti-insect and anti-parasitic active ingredient, can be distributed over an animal's hair, without the need for it to reach the skin in order to be effective.

The object of the present invention is to provide a single system wherein a composition, containing at least one (or more) active ingredients is (are) distributed homogeneously, in a localized manner and without leaking, onto at least one part of the body of a human or animal subject to be treated, particularly onto areas that are difficult to access, such as the ventral area of a dog.

Thanks to this system, the non-therapeutic treatment, by an active ingredient, of a human or animal subject makes it possible to prevent infestations by pests such as insects and parasites by a repellant action, while having a soothing and sometimes pain-killing effect, so as to produce a feeling of wellbeing in said subject.

Within the meaning of the invention, the feeling of "wellbeing" includes a relaxing, toning, soothing, de-stressing and even pain-killing effect.

Areas of skin that are "difficult to access" mean the areas of an animal's body covered by hair, particularly long hair, areas in which folds are continuously formed, or areas such as the lower abdomen, under the front legs (armpits), under the hind legs, etc.

A "flexible" container means a container made of a plastics material of which at least one part of its walls can be deformed under the action of a pressure exerted thereon, in order to extrude a controlled quantity of the suspension contained therein.

The first object of the present invention is therefore a combination of a container with a flexible wall and a generally homogenous suspension contained in said container, at least one orifice being made in a point of said container so as to achieve the evacuation of a controlled quantity of said suspension, said suspension comprising a continuous aqueous phase that forms 80 to 99.5% of its weight, characterized in that said aqueous phase can contain particulate solid supports, the amount sufficient to make up 100% consisting of an oily or lipophilic phase containing at least one active ingredient, the container also comprising an applicator consisting of friction members made of a polymer material, suitable for applying said suspension from the outlet of said orifice onto an area of the body of the subject to be treated, said suspension having an apparent suitable viscosity of between 1000 and 500000 centipoises, allowing it to be distributed homogeneously by said members of said applicator.

Advantageously, a homogenous, smoothing effect of the suspension is achieved on the area of the body of a human subject, and an untangling, smoothing effect is achieved on the hairs of the area of the body of an animal subject.

According to one embodiment, the suspension is a gel or a cream.

According to one embodiment, the applicator is a brush, the friction members of which are formed by a plurality of flexible teeth, spaced apart by an average distance of between 0.1 mm and 7 mm, teeth of a length of between 2 and 15 mm, and sufficiently flexible to untangle the hair of the animal to be treated, separate the hairs and also smooth said suspension over the hair.

According to a first variation, the plurality of teeth, taken as a whole, forms a row, the cross-sectional view of which resembles that of a cone that is suitable, during use, for an application onto the area of the body to be treated, if the container is held in a position forming an angle substantially equal to 90° in relation to the horizontal plane of the application site, and/or an angle substantially comprised between 30 and 45° in relation to the horizontal plane of the application site.

Advantageously, the structure of the row of teeth, substantially in the general form of a cone or roof, enables a good homogenous application of the suspension onto the areas of the body of the subject, even those that are difficult to access, particularly the ventral parts and between the legs of a dog for example. In any case, the teeth enable, by following a different angle of application, a good smoothing of said suspension over the hair and even a coating of the hairs.

According to a second variation, the teeth of the applicator can be stiffened, spaced apart and shortened so that they are suitable for the short hair of an animal and, to a lesser extent, for its sensitivity when passing the applicator over its skin; as the applicator comprises teeth of 3 to 5 mm long, spaced 4 to 5 mm apart, it is perfectly suitable for the treatment of a horse.

The container can have a variable volume, particularly in response to a pressure exerted on an adequate portion of the container. Thus, the container can be configured in the form of a tube with flexible walls, the variation in volume being the result of the pressure exerted on its walls, perpendicular to their median plane.

The applicator member, as well as the flexible container, are made of a polymer material chosen from the group formed by polyvinyl chloride, polyethylene, polypropylene, polyurethane, polyamide, polyethylene terephthalate or mixtures thereof.

According to another embodiment, 0.1 to 30% of the weight of the suspension, in its aqueous phase, comprises solid microparticles with an average grain size of between 1 µm and 1 mm. Advantageously, the microparticles can contain the active ingredient(s), the amount of which is between 0.5 and 35% by weight in relation to the total weight of the microparticles.

According to one embodiment, the microparticles of the suspension are chosen from lamellar clays, kaolinites, porous silicas, zeolites, polymers of plant origin, polymers giving absorbent matrices and belonging to the polyethylene family, ethylene copolymers, polyamides, copolyamides, polyurethanes, polymethyl sesquioxanes, polyvinyl chloride, polyesters, polylactic acid or mixtures thereof.

According to one embodiment, the active ingredient has an anti-pest action and is chosen from the group formed by essential oils, pyrethrins, pyrethrinoids, carbamates, formamidines, icaridin, DEET, plant extracts and macerates such as margosa extract, repellent plant oils, nictotinyl compounds and monoterpenic alcohols such as geraniol, linalool, citriodiol or mixtures thereof.

According to one embodiment, the active ingredient induces a feeling of wellbeing and is chosen from the group formed by essential oils, plant extracts, non-steroidal anti-inflammatory (NSAI) drugs, methyl salicylate and its derivatives and monoterpenic alcohols such as menthol, linalool, borneol or mixtures thereof.

Essential oils include, for example, essential oils of wintergreen, rosemary, lavandin, lavender, eucalyptus, peppermint, nepeta cataria, valerian, chamomile, mandarin, lemon, orange, coriander, clove, marjoram, grapefruit, pine, cajuput, citronelle, laurel, thyme and camphor.

The combination of the content and suspension as defined above is used, as a topical application, to bring pain relief to a human and animal subject.

The oily or lipophilic phase, which contains the active ingredient(s), is chosen from the group formed by plant oils, mineral oils, lipophilic plant resins, oleoresins, liquid paraffins or mixtures thereof; the active ingredient(s) being dispersed within said oily phase.

The aqueous phase contains, in addition to water, commonly used formulation additives such as a gelling agent, thickener, emulsifier, film-forming agent, surfactant, emollient, inert fillers, natural or synthetic fragrance, coloring, a preservative or mixtures thereof.

The combination according to the present invention enables the implementation of a non-therapeutic method of treatment to induce a feeling of wellbeing, to combat pests or the association of both in a human or animal subject, said combination consisting of a container with a flexible wall and a generally homogenous suspension contained in said container, at least one orifice being made in a point of said container so as to achieve the evacuation of said suspension in a controlled quantity, said suspension comprises a continuous aqueous phase that forms from 80 to 99.5% of its weight, said method involves applying, topically or onto the hair of an area of the body of said subject to be treated, said suspension of which said aqueous phase can contain particulate solid supports, the amount sufficient to make up 100% consisting of an oily or lipophilic phase containing at least one active ingredient, the container also comprising an applicator consisting of friction members made of polymer material, suitable for applying said suspension from the outlet of said orifice onto an area of the body of the subject to be treated, having an effect of smoothing and/or untangling in said area, which can undergo deformations due to the movements of said subject during the treatment, said suspension having a suitable apparent viscosity of between 1000 and 500000 centipoises, so as to be distributed homogeneously and without leaking by said members of said applicator.

Advantageously, the administration of the active ingredient is optimized and targeted since, according to the particular characteristics of the combination, it is possible to apply the active ingredient either onto the coat only, or onto the skin only, or onto both at the same time.

The applicator is a brush, the friction members of which are formed by a plurality of flexible teeth, spaced apart at an average distance of between 0.1 mm and 7 mm, teeth of a length of between 2 and 15 mm; and sufficiently flexible to untangle the hair of the animal to be treated, during use, separate the hairs and also smooth said suspension over the hair, depending on the application position of the applicator.

The plurality of teeth, taken as a whole, forms a row, the cross-sectional view of which resembles that of a cone that is suitable, during use, for an application onto the area of the body to be treated, if the container is held in a position forming angles substantially equal to 30°, 45° and 90° in relation to the horizontal plane of the application site.

It is possible to correlate the physical and chemical properties of the suspension with the mechanical properties of the brush-applicator. In fact, if the suspension contains an active ingredient for topical application that induces a feeling of wellbeing, it is preferable that its apparent average viscosity is greater than or equal to 150000 centipoises under the conditions previously described. In such a case, the teeth of the brush-applicator separate the hairs of the animal to be treated, which allows the suspension of suitable content, to achieve a better distribution and to reach the skin; the position of the container forming an angle substantially equal to 90° in relation to the horizontal plane of the application site.

If the suspension contains an anti-pest active ingredient and is to be applied onto the hair, it is preferable that its apparent average viscosity is less than or equal to 150000 centipoises. In such a case, during use, the content of the suspension allows a preferential distribution over the hairs of the animal to be treated; the position of the container forming an angle of between 30 and 45° in relation to the horizontal plane of the application site.

In its aqueous phase, the suspension contains 0.1 to 30% of its weight of solid microparticles with an average grain size of between 1 μm and 1 mm, said microparticles can contain the active ingredient(s) the amount of which is between 0.5 and 35% by weight in relation to the total weight of the microparticles.

The microparticles of the suspension are chosen from lamellar clays, kaolinites, porous silicas, zeolites, polymers of plant origin, polymers giving absorbent matrices and belonging to the polyethylene family, ethylene copolymers, polyamides, copolyamides, polyurethanes, polymethyl sesquioxanes, polyvinyl chloride, polyesters and polylactic acid or mixtures thereof.

The active ingredients are chosen from the group formed by essential oils, pyrethrins, pyrethrinoids, carbamates, formamidines, icaridin, DEET, plant extracts and macerates, non-steroidal anti-inflammatory (NSAI) drugs, nictotinyl compounds, methyl salicylate and its derivatives and monoterpenic alcohols such as geraniol, linalool, citriodiol, menthol or mixtures thereof.

The following examples are given purely by way of illustration, without limiting the scope of the present invention. A Brookfield DVII viscometer was used to measure the viscosity of the suspension.

Example 1

Formulation of a Homogenous Suspension for Topical Application on a dog.

TABLE 1

Composition of a gel containing active ingredients for topical application, which causes a feeling of wellbeing.

| Constituents | Function | Quantity (%) |
|---|---|---|
| Alkyl Acrylate (Carbopol ®) | Gelling Agent | 0.6 |
| Glycerin | Emollient | 10 |
| PEG-sorbitan monolaurate (KAOPAN ®) | Surfactant | 10 |
| Polyvinylpyrrolidone | Film-forming Agent | 2.5 |
| Gaultheria Essential Oil | Active Ingredient | 0.42 |
| Rosemary Essential Oil | Active Ingredient | 0.15 |
| Coconut Oil | Vector | 0.11 |
| Fragrance | Fragrance | 0.75 |
| Coloring | Coloring | 0.06 |
| Soda | pH Regulator | 0.24 |
| Water | Vector | qsp 100 |

Example 2

Formulation of a homogenous suspension containing microparticles, designed to combat parasitic insects on a dog. The microparticles are made of polyamide of which the average grain size is 300 μm.

TABLE 2

Composition of a gel containing microparticles loaded with anti-pest active ingredient for topical application on the hair.

| Constituents | Function | Quantity (%) |
|---|---|---|
| Alkyl Acrylate (Carbopol ®) | Gelling Agent | 0.3 |
| Glycerin | Emollient | 10 |
| PEG-sorbitan monolaurate (KAOPAN ®) | Surfactant | 10 |
| Polyvinylpyrrolidone | Film-forming Agent | 2.5 |
| Lavender Essential Oil | Active Ingredient | 2.78 |
| Geraniol | Active Ingredient | 1 |
| ORGASOLO ® microparticles 32% loaded with peppermint essential oil and 4% gaultheria essential oil, by weight of the total weight of the microparticles | Particulate solid support | 25 |
| Soda | pH Regulator | 0.23 |
| Water | Vector | qsp 100 |

The Single FIGURE shows a schematic cross-section, not to scale, of a reservoir-tube surmounted by a brush-applicator suitable for the distribution of the gel formulation defined in Tables 1 and 2.

This FIGURE shows a container in the form of a reservoir-tube (1) made of polyethylene, the walls of which are flexible. The body of the reservoir-tube (1) extends into a bottleneck (4) 35 mm in diameter, which is surmounted by a brush-applicator (2) in the center of which is arranged an outlet orifice (6) for the gel (3), an orifice that is 5 mm in diameter. The brush-applicator (2) consists of a plurality of teeth (5) arranged in 10 concentric circles of which the overall geometric form resembles the roof of a house. Within this row, the teeth round the peripheral edge have a length (L1) of 7 mm, while those located in the center have a length (L2) of 10 mm. The space between the teeth measures 1 mm.

From the constituents listed in Table 1, a homogenous suspension is obtained in the form of a gel, the viscosity of which is 368000 centipoises (with mobility of 64 at 20° C.) after manufacture. This gel is introduced into the reservoir-tube surmounted by a brush-applicator shown in FIG. 1. By squeezing the walls of the reservoir-tube, about a 2 g hazelnut-sized amount of gel is extruded; this is then applied onto the dog's abdomen by holding the reservoir-tube in a position forming an angle of 90° in relation to a horizontal plane, the brush-applicator being turned upwards. It will be noted that nothing leaks out during the application. Thanks to the brush-applicator, the dog's hairs are well separated for the application, which enables good adhesion of the gel mainly onto the skin of the ventral area.

From the constituents of Table 2, a gel is obtained with a viscosity of 90381 centipoises 3 days after manufacture. The anti-parasitic gel thus obtained is applied homogenously without leakage onto a dog's hairs, thanks to the brush-tube applicator described above.

The invention claimed is:

1. A combination of a container with a flexible wall and a generally homogenous suspension contained in said container, at least one orifice in said container being configured for the evacuation of a controlled quantity of said suspension, said suspension comprising
80% to 99.5% (w/w) of a continuous aqueous phase containing particulate solid supports, and
an oily or lipophilic phase containing at least one active ingredient, in an amount sufficient to make up 100% (w/w) of said suspension,
the container also comprising an applicator consisting of a plurality of flexible teeth that are made of a polymer material and arranged in concentric circles of progressively decreasing length, and which are suitable for applying said suspension exiting from said orifice onto an area of a body of a subject to be treated, said suspension having an apparent viscosity of between 1000 and 500000 centipoises, allowing said suspension to be distributed homogeneously by said plurality of flexible teeth of said applicator.

2. The combination according to claim 1, wherein the suspension is a gel or a cream.

3. The combination according to claim 1, wherein said applicator is a brush, and each of said plurality of flexible teeth is spaced apart from adjacent teeth by an average distance of between 0.1 mm and 7 mm.

4. The combination according to claim 3, wherein each of said plurality of flexible teeth are is of a length of between 2 and 15 mm, and wherein said plurality of flexible teeth are sufficiently flexible to untangle hairs, separate hairs and smooth said suspension over hairs.

5. The combination according to claim 1, wherein the each of said plurality of flexible teeth is stiffened, spaced 4 to 5 mm apart and has a length of 3 to 5 mm.

6. The combination according to claim 1, wherein the active ingredient induces a feeling of wellbeing and is chosen from essential oils, plant extracts, non-steroidal anti-inflammatory (NSAI) drugs, methyl salicylate and its derivatives and monoterpenic alcohols.

7. The combination according to claim 1, wherein the active ingredient has an anti-pest action and is chosen from essential oils, pyrethrins, pyrethrinoids, carbamates, formamidines, icaridin, DEET, a plant extract[s], a plant macerate a repellent plant oil, a nictotinyl compound, a monoterpenic alcohol or mixtures thereof.

8. The combination according to claim 1, wherein said particulate solid supports, in said continuous its-aqueous phase, are 0.1 to 30% (w/w) of said suspension and are solid microparticles with an average particle size of between 1 μm and 1 mm.

9. The combination according to claim 8, wherein each of the microparticles contains a further active ingredient in an amount of between 0.5 and 35% by weight in relation to the total weight of that microparticle.

10. The combination according to claim 1, wherein the particulate solid supports are microparticle.

11. The combination according to claim 10, wherein said microparticles are microparticles of lamellar clays, microparticles of kaolinites, microparticles of porous silicas, microparticles of zeolites, microparticles of polymers of plant origin, or microparticles of a polymer giving an absorbent matrix.

12. The combination according to claim 7, wherein said plant extract is a margosa extract.

13. The combination according to claim 7, wherein said monoterpenic alcohol is geraniol, linalool, citriodiol, or combinations thereof.

14. The combination according to claim 11, wherein said polymer is a polyethylene, an ethylene copolymer, a polyamide, a copolyamide, polyurethanes, a polymethyl sesquioxane, a polyvinyl chloride, a polyester, a polylactic acid or mixtures thereof.

* * * * *